Figure 1:
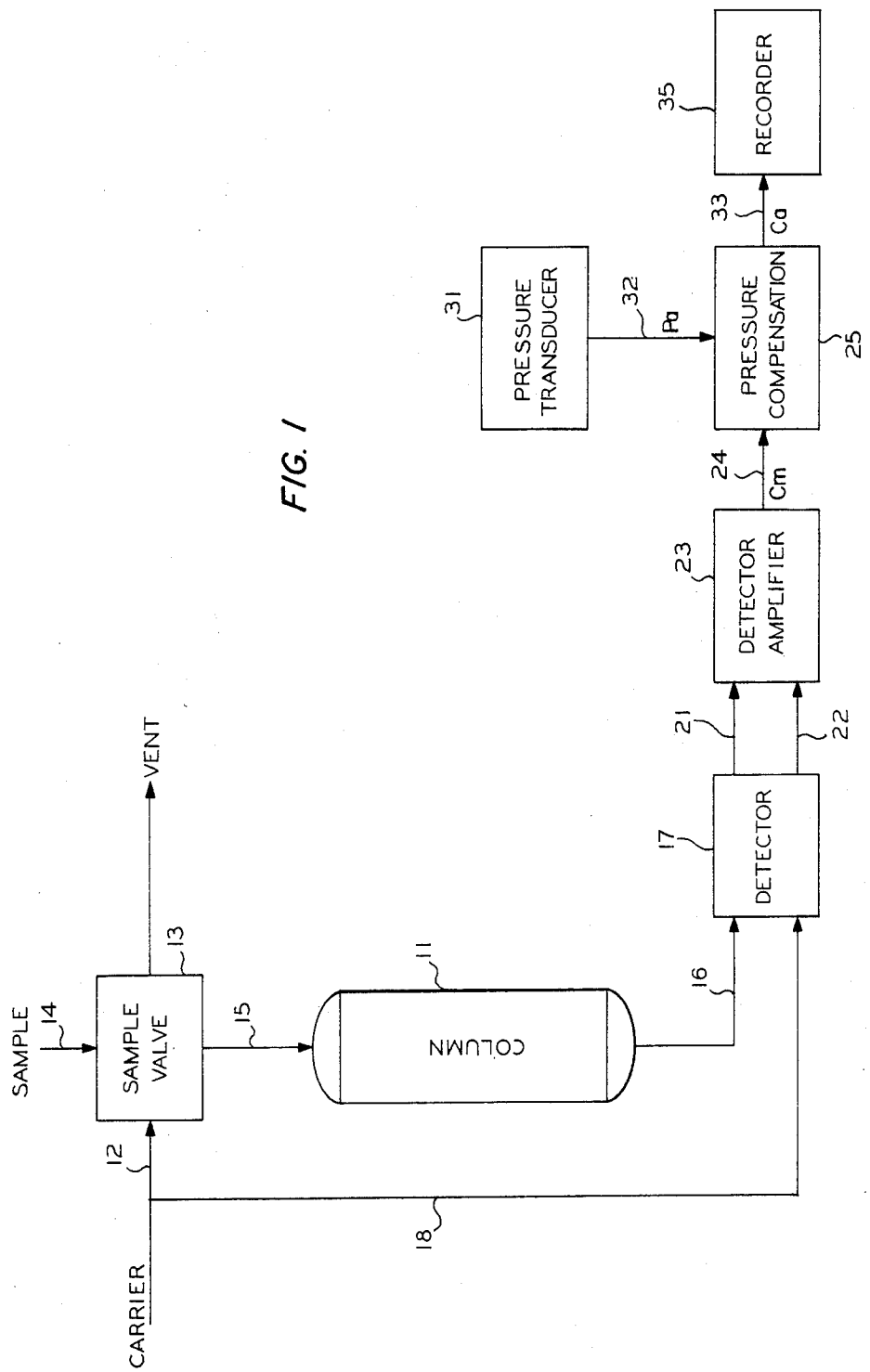

United States Patent [19]

Ayers et al.

[11] Patent Number: 4,512,181

[45] Date of Patent: Apr. 23, 1985

[54] PRESSURE COMPENSATION FOR A CHROMATOGRAPH

[76] Inventors: Buell O. Ayers; Edwin K. Clardy, both of c/o Phillips Petroleum Company, Bartlesville, Okla. 74004

[21] Appl. No.: 467,547

[22] Filed: Feb. 17, 1983

[51] Int. Cl.³ ............................................ G01N 31/08
[52] U.S. Cl. ......................................................... 73/23.1
[58] Field of Search ................. 73/23.1, 1 G; 364/498, 364/558

[56] References Cited

U.S. PATENT DOCUMENTS

| 2,964,938 | 12/1960 | Fuller | 73/23.1 |
| 3,057,184 | 10/1962 | Spracklen | 73/23.1 |
| 3,240,052 | 3/1966 | Reinecke et al. | 73/23.1 |
| 3,283,563 | 11/1966 | Turner et al. | 73/23.1 |
| 4,141,237 | 2/1979 | DeFord et al. | 73/23.1 |
| 4,196,612 | 4/1980 | Clardy et al. | 73/23.1 |

OTHER PUBLICATIONS

B. O. Ayers et al., "Effects of Changes in Atmospheric Pressure on Gas Chrom. Output Signals", Report No. 116-81, pp. 1-32.

1981 Abstracts Pittsburgh Conference on Analytical Chemistry and Applied Spectroscopy, Mar. 9, 1981, No. 264.

Primary Examiner—Stephen A. Kreitman

[57] ABSTRACT

In a chromatographic analysis, errors in the chromatographic analysis caused by barometric pressure variations are corrected by dividing the actual measured analysis ($C_m$) by a correction factor which is calculated based on the actual atmospheric pressure at the time the measurement is made ($P_a$), the atmospheric pressure at which the chromatographic analyzer system was calibrated, and the slope of a plot of $C_m/C_a$ as a function of $P_a/P_c$ where $C_a$ is the magnitude that $C_m$ would have if errors were not introduced by changes in barometric pressure.

6 Claims, 2 Drawing Figures

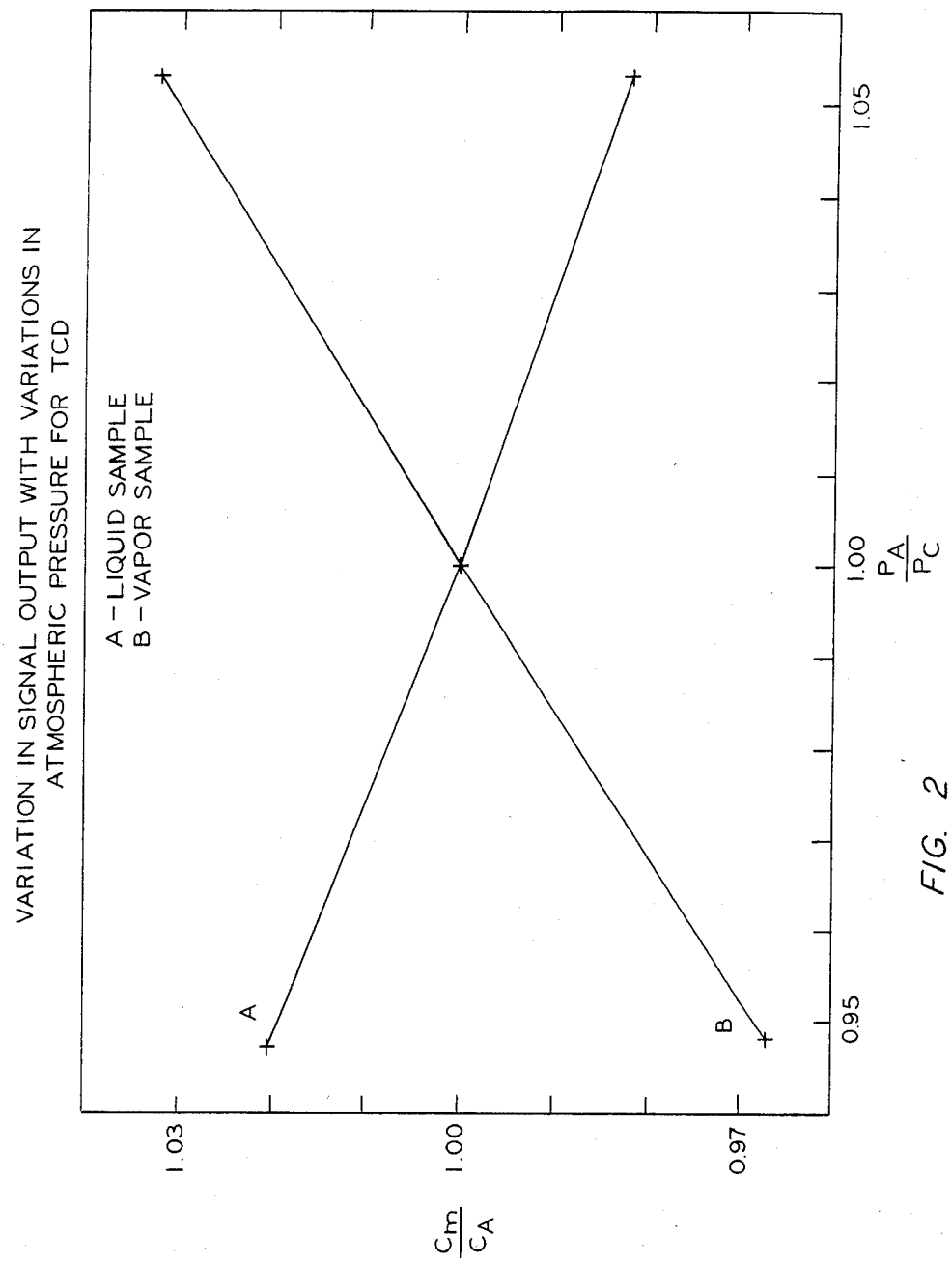

PRESSURE COMPENSATION FOR A CHROMATOGRAPH

This invention relates to chromatography. In a particular aspect this invention relates to method and apparatus for correcting errors in a sample analysis caused by barometric pressure variations.

A chromatograph is an analytical instrument that is used to individually detect the constituents of a sample to be analyzed. The chromatograph typically includes an analytical column through which a carrier fluid is passed continuously. The sample to be analyzed is injected into the carrier stream and is thus carried through the analytical column. The sample constituents are absorbed on the packing material in the analytical column at different affinities and are eluted from the column at different points in time.

A detector is employed to detect the separated constituents and the detector output signal can be plotted as a function of time to produce what is termed a chromatogram. As each sample component is eluted from the column it produces a sharp increase in the detector output signal amplitude which appears as a peak or spike in the chromatogram.

Small errors in the sample component analysis may result from changes in ambient atmospheric pressure in the immediate area of the chromatographic system. In many systems, if a sample valve is used to measure a definite volume of sample and to inject the sample into the carrier fluid, a change in ambient atmospheric pressure (barometric pressure) influences the mass of the sample taken for analysis because the sample in the sample valve is at a pressure which is a function of atmospheric pressure. A change in ambient atmospheric pressure will also influence the height and area of the peaks which are representative of the sample components because the carrier velocity at the column outlet is also dependent on atmospheric pressure.

It is common practice to correct or compensate for any errors that may result from changes in ambient atmospheric pressure. One technique which may be used is to simply recalibrate whenever changes in atmospheric pressure occur. However, this is typically not practical in a plant operation.

Another technique utilized is normalizing the chromatograph output. The area of the output peak resulting from each individual component is divided by the total area of all peaks to normalize the chromatograph output and in this manner errors caused by changes in ambient atmospheric pressure are corrected. However, normalization of the output of a chromatograph is often time consuming and sometimes cannot be performed. A total analysis of all the components of the sample is usually required before normalization of the peak signals can be carried out. When only two or three components of a sample having many more components are to be analyzed, a compensation for atmospheric pressure variations can be more desirable than normalization of the chromatograph output. Compensation for atmospheric pressure variations may also be desirable where the analysis must be performed in a short length of time.

Other methods include the use of a pressure regulator such as is disclosed in U.S. Pat. No. 4,196,612 or the use of analog electronics to apply compensation as disclosed in U.S. Pat. No. 4,141,237. However, while both of these methods are excellent methods for pressure compensation, the requirement of a pressure regulator requires additional equipment and analog circuits are notoriously subject to drift because of temperature variations.

It is thus an object of this invention to provide method and apparatus for correcting errors in a sample analysis caused by barometric pressure variations which avoids problems which have been encountered in previous pressure compensation techniques.

In accordance with the present invention, it has been found that the relationship between the actual measured output from a chromatographic analyzer system ($C_m$), such as a peak height or a peak area or a concentration or other value obtained by multiplying a peak height or peak area by some constant, and the chromatographic analyzer output ($C_a$) which would have been provided if the measurement had been made at the atmospheric pressure at which the chromatographic analyzer system was calibrated is given by Equation 1:

$$\frac{C_m}{C_a} = 1 + M\left(\frac{P_a}{P_c} - 1\right) \qquad (1)$$

where:

$P_a$ is the actual atmospheric pressure at the time the measurement is made;

$P_c$ is the atmospheric pressure at which the chromatographic analyzer system was calibrated; and $M$ is the slope of a plot of $C_m/C_a$ as a function of $P_a/P_c$.

It has further been found that once this relationship is established for any particular detector, the same relationship hold for a wide variation in conditions such as different flow rates, temperatures, etc. Thus, in accordance with the present invention, a correct output from a chromatographic analyzer system is obtained by dividing the measured output such as peak height or peak area by the expression $$1 + M\left(\frac{P_a}{P_c} - 1\right)$$

In this manner, a corrected output is obtained quickly and a single pressure measurement signal may be utilized to apply a correction factor to the output from a plurality of chromatographic analyzers located in a plant which is especially desirable in the situation where the plurality of chromatographic analyzers are tied into a central computer.

Other objects of the invention will be apparent from the foregoing brief description of the invention and the claims as well as the detailed description of the drawings which are briefly described as follows:

FIG. 1 is an illustration of a chromatographic analysis system with pressure compensation added; and FIG. 2 is a plot of $C_m/C_a$ as a function of $P_a/P_c$.

The invention is described in terms of a typical chromatographic analysis system where a sample valve is utilized and the output is provided to a recorder. The invention is, however, not limited to this configuration but is applicable to any chromatographic analyzer configuration where pressure compensation is desired. The invention is also described in terms of electrical signals but is applicable to other types of signals such as pneumatic.

As used in this disclosure the term pressure refers to absolute pressure.

Referring now to the drawings and in particular to FIG. 1, there is shown a chromatographic column 11. A carrier fluid is introduced through conduit means 12 into sample valve 13. A sample of a fluid to be analyzed is delivered to sample valve 13 through conduit means 14. A conduit means 15 extends between sample valve 13 and the inlet to chromatographic column 11. A conduit means 16 extends between the outlet of chromatographic column 11 and the first inlet of a detector means 17. Carrier fluid is passed through the reference portion of detector means 17 by being introduced into the second inlet of detector means 17 through conduit means 18 which communicates with conduit means 12. Carrier fluid also flows through sample valve 13 and chromatographic column 11 to the fluid inlet of detector means 17.

At the beginning of an analysis period, sample valve 13 is actuated to introduce a predetermined volume of sample into the carrier fluid flowing through chromatographic column 11. The constituents of the sample are eluted in sequence and flow from chromatographic column 11 through conduit means 16 to the sample portion of detector means 17.

Detector means 17 establishes a differential output by establishing an electrical signal 21 representative of the composition of the carrier fluid carrying the sample passing through the sample portion of detector means 17 and an electrical signal 22 representative of the composition of the carrier fluid only in the reference portion of detector means 17. Signals 21 and 22 are then compared by detector amplifier 23 to produce signal 24 representative of a chromatographic analyzer output signal. Signal 24 is supplied to the pressure compensation system 25.

The pressure transducer 31 provides an output signal 32 which is representative of the actual atmospheric pressure at the time a measurement is taken. Signal 32 is provided as a second input to the pressure compensation system 25. The pressure compensation system 25 operates on signal 24, as will be more fully described hereinafter, to produce signal 33 which is representative of the atmospheric pressure compensated chromatographic analyzer output signal. In this preferred embodiment, signal 33 is supplied to recording means 35 where it is stored.

Referring now specifically to the pressure compensation system 25, the pressure compensation is preferably carried out by means of a digital computer such as the computer of the Optichrom ®2100 chromatographic analyzer system manufactured by Applied Automation, Inc., Bartlesville, Okla. Essentially, signal 24 is representative of the term $C_m$ in Equation 1, signal 33 is representative of $C_a$ and signal 32 is representative of $P_a$. The calibration pressure $P_c$ will be known. Thus, in order to determine $C_a$ based on Equation 1 it is necessary to know only the slope M. The derivation of the slope M for a thermal conductivity detector is discussed hereinafter.

FIG. 2 illustrates a plot of $C_m/C_a$ as a function of $P_a/P_c$ for a thermal conductivity detector. Line A is for a sample which is liquid in the sample loop and line B is for a sample which is vapor in the sample loop. The slope of the two lines are opposite indicating the extreme difference in the effect of pressure changes on a chromatographic analyzer system depending upon the type of sample. It is noted that a sample which is liquid in the sample loop must be converted to a vapor prior to passage through the chromatographic column as is well known.

The plots illustrated in FIG. 2 may be derived theoretically or by experimentation. However, once derived, the slope M remains substantially constant for all chromatographic analyzer systems which employ a thermal conductivity detector regardless of variations such as changes in flow rate, temperature, etc.

It is preferred to derive the slope M by experimentation and thus only an experimental derivation will be discussed hereinafter. The experimental values may be obtained by operating the chromatographic analyzer system at different atmospheric pressures which occur naturally, using a sample which has a known concentration of some component or which has some other known values such as a BTU value. Thus, for Equation 1 which is the equation of lines A and B, $C_a$ and $P_c$ will be known and $C_m$ and $P_a$ can be measured. A few data points will give the lines illustrated in FIG. 1 since the lines are substantially straight.

If one does not wish to make measurements at different atmospheric pressures, a chromatographic analyzer system using an absolute back pressure regulator such as that illustrated in U.S. Pat. No. 4,196,612 may be utilized to make the measurements. The pressure at which the absolute back pressure regulator is set may be changed to effectively change the pressure seen by the chromatographic analyzer system. For some detectors, such as a flame ionization detector, it is difficult to simulate changes in atmospheric pressure using an absolute back pressure regulator and thus, for such detectors, it may be necessary to obtain the slope M by operating the chromatographic analyzer system at different atmospheric pressures.

For a thermal conductivity detector, the slope of the plot B illustrated in FIG. 2 for a sample which is a vapor in the sample loop is about 0.62 while the slope of the line A for a sample which is a liquid in the sample loop is about $-0.36$.

The following example is presented to further illustrate the invention.

EXAMPLE

Data presented in Table I was obtained using the chromatographic analyzer system described in U.S. Pat. No. 4,196,612 and the data in Table I corresponds to the data set forth in Table 1 of that patent. The known BTU content of the gas analyzed was 1,112 BTU. The chromatographic analyzer system was calibrated at 798 mm of mercury.

TABLE I

| Run | BAROMETRIC PRESSURE mm Hg | CHROMATOGRAPHIC ANALYZER OUTPUT (BTU/ft³) | |
|---|---|---|---|
| | | Pressure Regulated | Pressure Not Regulated |
| 1 | 722 | 1112.4 | |
| 2 | 722 | 1111.8 | |
| 3 | 722 | 1112.6 | |
| 4 | 722 | 1112.1 | |
| 5 | 722 | 1114.6 | |
| 6 | 722 | 1112.3 | |
| 7 | 722 | 1112.6 | |
| 8 | 722 | 1114.4 | |
| 9 | 722 | 1114.5 | |
| 10 | 760 | 1113.0 | 1078.9 |
| 11 | 760 | 1113.0 | 1081.2 |
| 12 | 760 | 1112.6 | 1080.2 |
| 13 | 760 | 1112.1 | 1082.4 |

TABLE I-continued

| Run | BAROMETRIC PRESSURE mm Hg | CHROMATOGRAPHIC ANALYZER OUTPUT (BTU/ft³) | |
|---|---|---|---|
| | | Pressure Regulated | Pressure Not Regulated |
| 14 | 760 | 1112.9 | 1081.6 |
| 15 | 760 | 1113.1 | 1078.8 |
| 16 | 760 | 1112.0 | 1083.6 |
| 17 | 760 | 1112.7 | 1078.9 |
| 18 | 760 | 1112.2 | 1078.8 |
| 19 | 798 | | 1113.0 |
| 20 | 798 | | 1113.0 |
| 21 | 798 | | 1112.6 |
| 22 | 798 | | 1112.1 |
| 23 | 798 | | 1112.9 |
| 24 | 798 | | 1113.1 |
| 25 | 798 | | 1112.0 |
| 26 | 798 | | 1112.7 |
| 27 | 798 | | 1112.1 |

It can be seen from Table I that the back pressure regulation of U.S. Pat. No. 4,196,612 was effective to prevent changes in barometric pressure from substantially affecting the output from the chromatographic analyzer system. However, when the pressure was not regulated, it can be seen that there was a substantial variation in the BTU value measured when the barometric pressure was 760 mm of mercury.

Applying the pressure compensation of the present invention to Run 10 as an example, $P_a$ is equal to 760 mm of mercury and $P_c$ is equal to 798 mm of mercury. Thus, $P_a/P_c$ is equal to 0.95. The term $(P_a/P_c - 1)$ is thus equal to $-0.05$ and, since M for a sample which is a gas in the sample loop and a thermal conductivity detector is approximately 0.62, the term $M(P_a/P_c - 1)$ becomes $-0.031$. The term $1 - M(P_a/P_c - 1)$ is thus equal to 0.69. When this factor is divided into 1078.9, which was the measured BTU value for Run 10, the result is 1113.4 which is closely related to the actual BTU value of 1112.

A particular advantage to the present invention is the fact that the factor 0.69, as derived in the example, can be utilized to correct the output from a plurality of chromatographic analyzer systems which are operating in the same plant and which are analyzing samples which are a gas in the sample loop since these analyzers will be operating at essentially the same atmospheric pressure and can be calibrated at the same atmospheric pressure. Thus, the pressure compensation of the present invention is particularly applicable to systems in which a plurality of chromatographic analyzers are controlled by a single computer such as in the Optichrom ®2100 Chromatographic Analyzer System manufactured by Applied Automation, Inc., Bartlesville, Okla.

The invention has been described in terms of a preferred embodiment as illustrated in FIG. 1. The chromatographic analyzer system is a standard chromatographic analyzer system such as would be supplied by Applied Automation, Inc. with the Optichrom ®2100 Chromatographic Analyzer System or as the Optichrom ®102 Process Gas Chromatograph System. A pressure transducer which may be used is the GS-47 Pressure Transducer manufactured by Gulton Industries.

While the invention has been described in terms of the presently preferred embodiment, reasonable variations and modifications are possible by those skilled in the art and such variations and modifications are within the scope of the described invention and the appended claims.

That which is claimed is:

1. In a chromatographic analyzer system for analyzing the composition of a sample, wherein said chromatographic analyzer system has a detector means for providing an output signal ($C_m$) having an amplitude which varies as a function of time in accordance with the sample composition and wherein said chromatographic analyzer system is calibrated at a barometric pressure $P_c$, the improvement comprising apparatus for compensating for errors in said output signal, said errors being produced by changes in barometric pressure from the barometric pressure $P_c$, said apparatus comprising:

means for establishing a first signal representative of the actual barometric pressure ($P_a$) at the time an analysis is made using said chromatographic analyzer system;

means for determining the slope (M) of a plot of $C_m$ divided by the magnitude that $C_m$ would have if errors were not introduced by changes in barometric pressure ($C_a$) as a function of $P_a/P_c$ for said detector means and for said sample;

means for calculating a pressure compensation factor using $P_c$, $P_a$ and M; and means for dividing said output signal by said pressure compensation factor to compensate for errors in said output signal produced by changes in barometric pressure from the barometric pressure $P_c$.

2. Apparatus in accordance with claim 1 wherein said pressure compensation factor is equal to $1 + M(P_a/P_c - 1)$.

3. Apparatus in accordance with claim 2 wherein said means for determining the slope (M) comprises:

means for analyzing a sample having a known composition at a plurality of different barometric pressures, as seen by said chromatographic analyzer system, to establish the values required for said plot; and means for calculating the slope of the experimentally determined plot.

4. A method for compensating for errors in the output signal ($C_m$) from the detector associated with a chromatographic analyzer system used to analyze the composition of a sample, wherein said errors are caused by changes in barometric pressure with respect to the barometric pressure ($P_c$) at which said chromatographic analyzer was calibrated and wherein said output signal has an amplitude that varies as a function of time in accordance with the composition of said sample, said method comprising the steps of:

establishing a first signal representative of the actual barometric pressure ($P_a$) at the time an analysis is made using said chromatographic analyzer system;

determining the slope (M) of a plot of $C_m$ divided by the magnitude that $C_m$ would have if errors were not introduced by changes in barometric pressure ($C_a$) as a function of $P_a/P_c$ for said detector means and for said sample;

calculating a pressure compensation factor using $P_c$, $P_a$ and M; and dividing said output signal by said pressure compensation factor to compensate for errors in said output signal produced by changes in barometric pressure from the barometric pressure $P_c$.

5. A method in accordance with claim 4 wherein said pressure compensation factor is equal to $1 + M(P_a/P_c - 1)$.

6. A method in accordance with claim 5 wherein said step of determining the slope (M) comprises:

analyzing a sample having a known composition at a plurality of different barometric pressures, as seen by said chromatographic analyzer system, to establish the values required for said plot; and calculating the slope of the experimentally determined plot.

* * * * *